(12) United States Patent
Tabada et al.

(10) Patent No.: US 8,738,110 B2
(45) Date of Patent: May 27, 2014

(54) RIGID SPINE REINFORCED POLYMER MICROELECTRODE ARRAY PROBE AND METHOD OF FABRICATION

(75) Inventors: Phillipe Tabada, Roseville, CA (US); Satinderpall S. Pannu, Pleasanton, CA (US)

(73) Assignee: Livermore National Security, LLC, Livermore, CA (US)

( * ) Notice: Subject to any disclaimer, the term of this patent is extended or adjusted under 35 U.S.C. 154(b) by 50 days.

(21) Appl. No.: 12/772,895

(22) Filed: May 3, 2010

(65) Prior Publication Data

US 2010/0331935 A1    Dec. 30, 2010

Related U.S. Application Data

(60) Provisional application No. 61/174,817, filed on May 1, 2009.

(51) Int. Cl.
*A61B 5/0478* (2006.01)

(52) U.S. Cl.
USPC .......................................... 600/378; 607/116

(58) Field of Classification Search
USPC .............. 600/377–378; 607/55–57, 115–125
See application file for complete search history.

(56) References Cited

U.S. PATENT DOCUMENTS

| 4,461,304 A * | 7/1984 | Kuperstein | 600/378 |
| 7,190,989 B1 * | 3/2007 | Swanson et al. | 600/378 |
| 8,386,006 B2 * | 2/2013 | Schouenborg | 600/373 |

* cited by examiner

*Primary Examiner* — Rex R Holmes
(74) *Attorney, Agent, or Firm* — James S. Tak

(57) ABSTRACT

A rigid spine-reinforced microelectrode array probe and fabrication method. The probe includes a flexible elongated probe body with conductive lines enclosed within a polymeric material. The conductive lines connect microelectrodes found near an insertion end of the probe to respective leads at a connector end of the probe. The probe also includes a rigid spine, such as made from titanium, fixedly attached to the probe body to structurally reinforce the probe body and enable the typically flexible probe body to penetrate and be inserted into tissue, such as neural tissue. By attaching or otherwise fabricating the rigid spine to connect to only an insertion section of the probe body, an integrally connected cable section of the probe body may remain flexible.

4 Claims, 9 Drawing Sheets

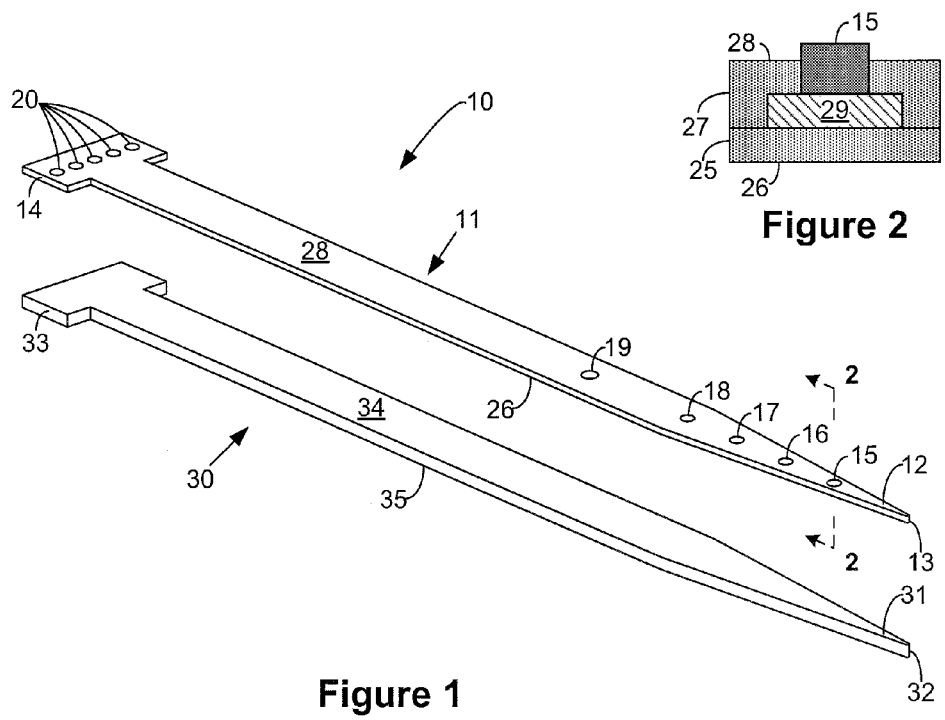
Figure 1
Figure 2
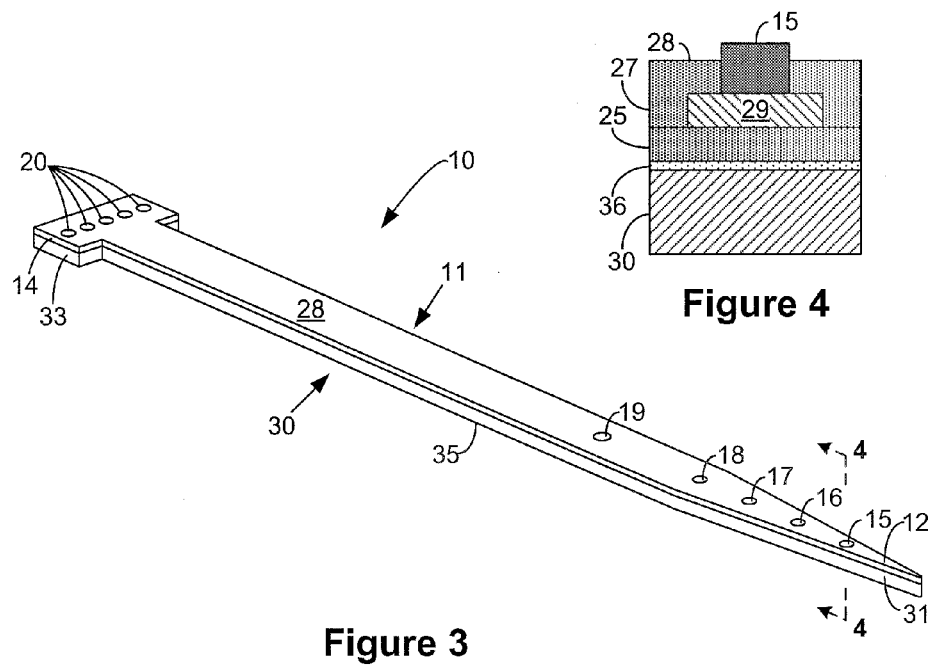
Figure 3
Figure 4

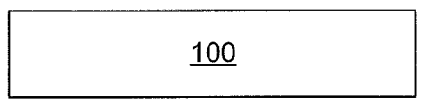
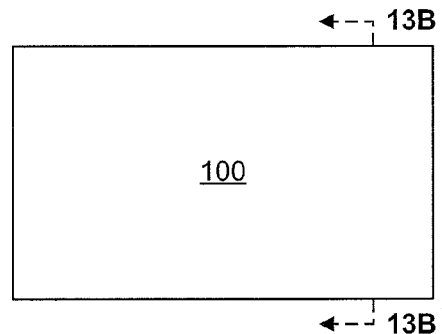
Figure 13B          Figure 13A
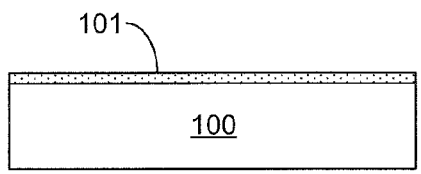
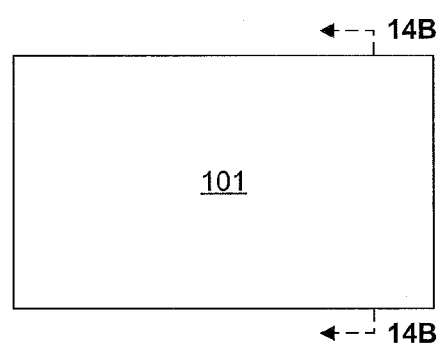
Figure 14B          Figure 14A
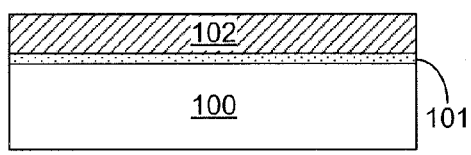
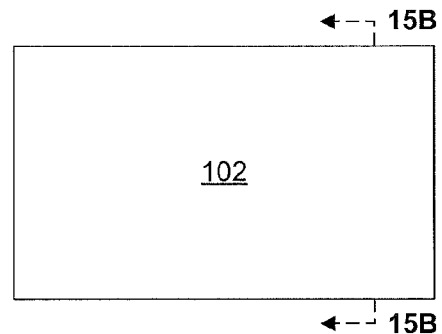
Figure 15B          Figure 15A

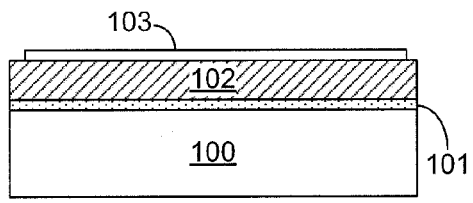 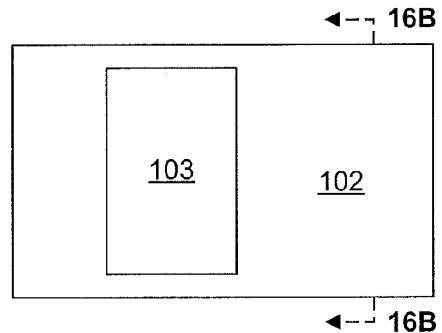
Figure 16B  Figure 16A
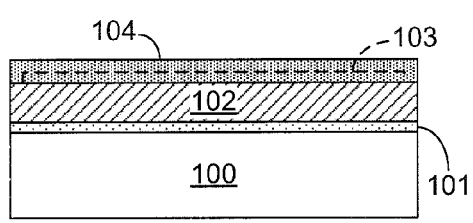 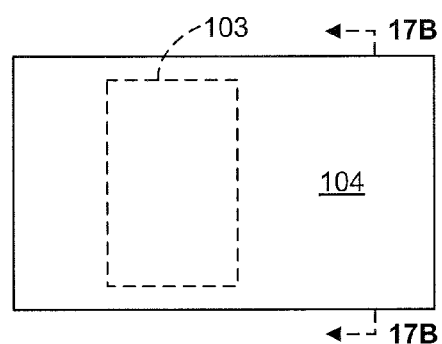
Figure 17B  Figure 17A
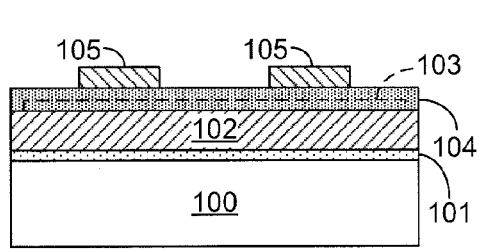 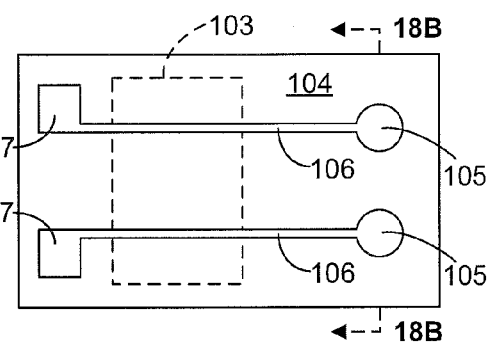
Figure 18B  Figure 18A

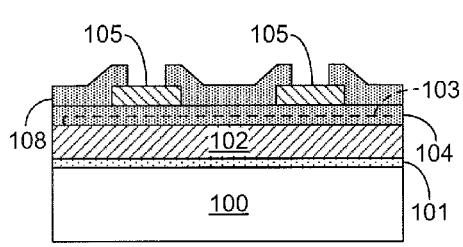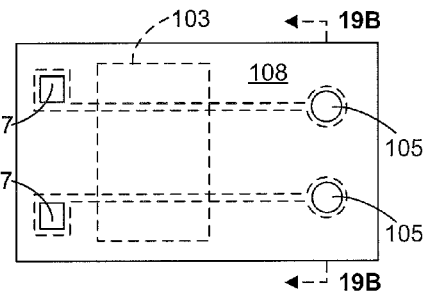
Figure 19B                Figure 19A
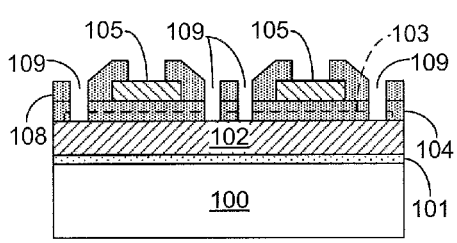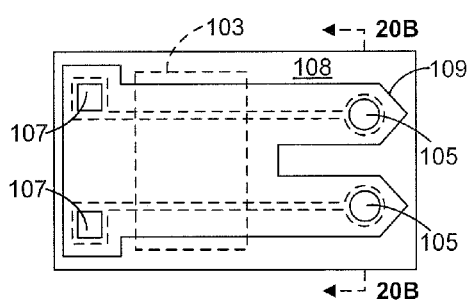
Figure 20B                Figure 20A
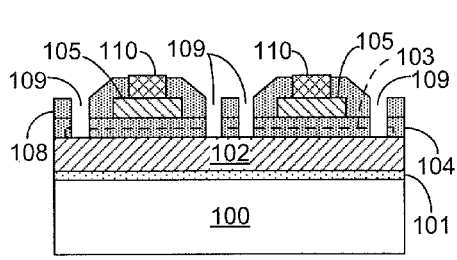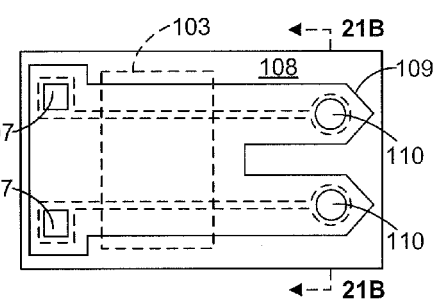
Figure 21B                Figure 21A

RIGID SPINE REINFORCED POLYMER MICROELECTRODE ARRAY PROBE AND
METHOD OF FABRICATION

CLAIM OF PRIORITY IN PROVISIONAL APPLICATION

This application claims priority in provisional application filed on May 1, 2009, entitled "Titanium Based Fabrication of Rigid Microelectrode Array with Flexible Cabling and Packaging Regions" Ser. No. 61/174,817, by Phillipe J. Tabada et al, and incorporated by reference herein.

FEDERALLY SPONSORED RESEARCH OR DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to the field of thin film microprobes and fabrication methods, and more particularly to microelectrode array probes having rigid spines which provide structural reinforcement to at least a portion of a probe body to enable at least the reinforced portions to resist bending and buckling, especially during insertion.

BACKGROUND OF THE INVENTION

Microelectrode neural probes are an essential tool in neuroscience. They provide a direct electrical interface with the neurons of a biological entity's nervous system. Such neural probes can target the neuronal activity of neurons, enabling researchers and clinicians to better explore and understand neurological diseases, neural coding, neural modulations, and neural topologies. Moreover, the ability to analyze neuronal activity using neural probes has led to the development of new neuro-therapeutic devices implemented through brain-machine interfaces. These interfaces use neural probes implanted to bypass damaged tissue and stimulate neural activity, so that a patient can regain lost communication and/ or control with respect to some aspect of the patient's nervous system.

One of the most recent types of neural probes are thin-film micromachined probes fabricated on silicon substrates using MEMS fabrication techniques. Signal recording sites of such silicon probes typically comprise exposed metal pads located on rigid silicon shanks that are connected, via interconnection traces, to output leads or to signal processing circuitry on a monolithic substrate. Silicon is the most widely used substrate for this type of microprobe because of its unique physical characteristics and widespread use in the microelectronics industry. These probes generally provide more control over the size and electrical properties of the recording and stimulating sites or drug delivery channels. Furthermore the silicon substrate allows integration of active circuitry that improves the quality of recording and stimulation applications as well as sensors, actuators, and even valves.

Despite the advantages of using a silicon substrate for neural probes, concerns exist about the mechanical strength of silicon substrate and its suitability for chronic biological applications due to the fact that bulk silicon substrate is a hard, fragile, brittle material and subject to breakage, especially during insertion where a silicon probe can break into several large or small pieces at the point of fracture. In case of a fracture, there is some risk that small pieces of silicon might remain in and damage the neural tissue or might migrate down into the brain. Even if the surgeon removes the body of the microprobe, he/she might not see all small fragments or may cause significant damage to the surrounding tissue if he/she tries to pull them out, since they usually have several sharp edges. Even if multiple insertions and removals are possible, the use of silicon may still remain a safety issue due to accumulated stress, fatigue, and microfractures from the prior insertions and removals.

Attempts to increase the mechanical strength of silicon probes have involved making the probe thicker and wider, which can also be problematic because of the possibility of severing or otherwise damaging the nerve tissue. In particular, the probe width and thickness cannot be increased to more than a few tens of microns due to risk of physical tissue damage. And another method of attempting to mitigate this risk of silicon breakage is to make the substrate of the microelectrode array flexible by utilizing thin-metal electrode sites and enclosing the wiring between polymer materials. The resulting electrode array is completely flexible, thereby providing needed strain relief. However, this design prevents direct insertion of the probe into brain tissue. Instead, with this type of probe, an incision much be first created to effect implantation. This typically results in increased tissue damage. Still other example approaches are disclosed in U.S. Pat. Pub. No. 2005/0107742 disclosing a shatter-resistant microprobe, and U.S. Pat. Pub. No. 2009/0299166 disclosing a MEMS flexible substrate neural probe.

What is needed is a microelectrode array probe that is sufficiently resistant to fracture and breakage into independent pieces upon insertion and implantation, especially one that is capable of withstanding multiple insertions and removals without buckling and breakage, i.e. having a buckling strength that is significantly greater than the force needed to penetrate that specific tissue and overcome the friction applied to the moving probe shank during insertion and removal. Furthermore, it would be advantageous to provide a microelectrode array probe capable of mitigating tissue damage during implantation, and that also can be relatively easily and efficiently fabricated in large numbers.

SUMMARY OF THE INVENTION

One aspect of the present invention includes a microelectrode array probe comprising: an elongated probe body having a plurality of conductive lines enclosed within a polymeric material and extending from a connector end of the probe body toward an insertion end of the probe body, and a plurality of microelectrodes connected by the plurality of conductive lines to corresponding leads at the connector end; and an elongated rigid spine fixedly connected to the probe body to structurally reinforce the probe body.

Another aspect of the present invention includes a thin film microelectrode array probe comprising: a first rigid spine layer; a second rigid spine layer at a removed location from the first rigid spine layer, said first and second rigid spine layers integrally formed as part of a monolithic rigid spine layer that is subsequently separated from each other by removing a mid section of the monolithic rigid spine layer connecting between the first and second rigid spine layers; a first insulating layer having a first end section formed on the first rigid spine layer, a second end section formed on the second rigid spine layer, and a mid section formed on a sacrificial layer previously formed between the mid section of the first insulating layer and the mid section of the monolithic rigid spine layer, but now removed to effect the removal of the mid-section of the monolithic rigid spine layer; an array of at least one conductive line formed on the first insulating layer so that each conductive line extends across the mid section of the first insulating layer and terminates at conductive pads formed at the first and second end sections; and a second insulating layer formed over the array to surround and insulate the array while leaving the conductive pads exposed, whereby the first rigid spine layer rigidly supports the conductive pads formed at the first end section, the second rigid spine layer rigidly supports the conductive pads formed at the second end section, and sections of the array, the first insulating layer, and the second insulating layer that are located along the mid-section of the first insulating layer are flexible.

Another aspect of the present invention includes a method of fabricating a microelectrode array probe comprising: providing a rigid spine layer; forming a sacrificial layer on a mid region of a deposition surface of the rigid spine layer while leaving opposing end regions of the deposition surface exposed; forming a first insulating layer over the sacrificial layer and the opposing end regions; forming an array of at least one conductive line on the first insulating layer so that each conductive line extends above and across the sacrificial layer and terminates at conductive pads above the opposing end regions; forming a second insulating layer over at least a portion of the array that extends above and across the sacrificial layer to surround and insulate at least that portion of the array; patterning the rigid spine layer to form opposing end sections that are detached from each other and from a mid section therebetween that is in contact with the sacrificial layer, wherein the opposing end sections substantially include the opposing end regions of the deposition surface and the mid section substantially includes the mid region of the deposition surface; and removing the sacrificial layer so as to remove the mid section of the rigid spine layer from between the opposing end sections and thereby enable flexible movement between two connector ends each rigidly supported by one of the opposing end sections of the rigid spine layer.

Another aspect of the present invention includes a method of fabricating a microelectrode array probe comprising: providing an elongated probe body having a plurality of conductive lines enclosed within a polymeric material and extending from a connector end of the probe body toward an insertion end of the probe body, and a plurality of microelectrodes connected by the plurality of conductive lines to corresponding leads at the connector end; and fixedly attaching an elongated rigid spine to the probe body to structurally reinforce the probe body.

Another aspect of the present invention includes a method of implanting a microelectrode array probe in tissue, comprising: providing an elongated probe body having a plurality of conductive lines enclosed within a polymeric material and extending from a connector end of the probe body toward an insertion end of the probe body, and a plurality of microelectrodes connected by the plurality of conductive lines to corresponding leads at the connector end; and an elongate elongated rigid spine fixedly bonded to the probe body with an adhesive that dissolves in the human body, said spine having a tab for handling the probe; inserting the probe into biological tissue; and after the adhesive is dissolved, handling the tab to remove the elongated rigid spine from the human body while the elongated probe body remains in the biological tissue.

Generally, the present invention is directed to a microelectrode array probe having an elongated rigid body spine, (e.g. made of titanium, for example) which structurally reinforces, braces, and otherwise supports an insertion section of a probe body (especially a flexible probe body), to increase the probe's buckling strength necessary for penetration and insertion into tissue without fracture and breakage. The elongated rigid spine enables the probe to have a thin/narrow profile which reduces risk of nerve damage when used for example in the stimulation or sensing of neural tissue.

The microelectrode array probe of the present invention generally has two main components, (1) an elongated probe body comprising a plurality of conductive lines (e.g. wire traces, tracks, or pathways) surrounded/enclosed by an electrically insulating material (e.g. a polymer) and which connect a plurality of microelectrodes located near an insertion end to corresponding leads located at a connector end, and (2) an elongated rigid spine fixedly connected (e.g. bonded) to the elongated probe body to structurally reinforce the probe body. Because many types of polymers having electrically insulating as well as elastomeric properties, and because the probe body is primarily constructed of such material, the elongated probe body is interchangeably characterized herein as either an insulating probe body, a polymeric probe body, and an elastomeric or flexible probe body especially if elastomeric insulators are used. In particular, various types of polymeric materials may be utilized for the elongated probe body, such as but not limited to Parylenes, polyamides, silicones, polycarbonates, polystyrene, polyurethane, SU-8, Poly(methyl methacrylate (PMMA), Zotek, etc. And the rigid spine is made from a suitably rigid material such as but not limited to titanium (all grades), stainless steel (all grades), aluminum, alumina, zirconium, zirconia, silicon, silicon dioxide, silica glass such as Pyrex 774, glass such as soda-lime, silicon carbide, quartz, quartzitic materials, sapphire, tungsten, tungsten carbide, cobalt-chrome alloys, nitinol, diamond, Yttrium-iron garnet, graphite, glass fiber reinforced plastic, carbon fiber reinforced composites or plastic, polycarbonates, polystyrene, polyurethane, etc.

Depending on whether the rigid spine is connected to all of the probe body or only a section of it (i.e. an insertion section), the probe may be fabricated as a wholly rigid probe, or having both a rigidly reinforced insertion section and a non-reinforced flexible cable section. In the latter case, the insertion section and the flexible cable section are monolithically formed and integrally connected together using an elastomeric insulating material (e.g. an elastomeric polymer), so as not to require an additional connection step to join the two sections together. This avoids having to electrically connect different sub-components that are fabricated separately, which can lead to reliability and longevity issues during operation and ultimately result in the shorting and failure of electrodes used for either stimulation or sensing. In either case, however, the connection of the rigid spine to the insertion section may be achieved either as part of a thin film fabrication process using the spine (i.e. a rigid material such as titanium) as an underlying substrate upon which the polymer probe body is fabricated, or as an attachment of two separately fabricated components together.

Furthermore, the connection between the spine and the insertion section may be designed to be either permanent or temporary. For example, in one exemplary embodiment a bio-adhesive of a type (such as polysaccharides) which loses its adhesion properties (e.g. dissolves) when placed in the body is used so that after enabling the probe to penetrate and be inserted into tissue, the spine alone may be removed while keeping the microelectrode array (that is carried by the probe body) implanted. For this case, a tab or handle may be optionally provided extending from/connected to the rigid spine so as to both facilitate handling and insertion of probe, as well as removal of the spine. This method of microelectrode array probe implantation involves first providing a probe having a spine adhered to the probe body with a releasable bio-adhesive, such as polysaccharides. After inserting and positioning the probe, the adhesive is allowed to dissolve so that the spine is detached from the probe body. Then the spine may be removed, such as by using the tab/handle. Related to the removability of the spine from the probe body, is the fabrication of the microelectrodes on opposite surfaces of the probe body, e.g. top and bottom surfaces. A spine that is releasably attached to a face of the probe body having an electrode will initially cover the electrode during insertion, but will subsequently expose the electrode upon detachment from the probe body. And furthermore, the probe of the present invention may also employ thin film fabrication techniques to produce additional convergence faces of the insertion tip. In particular, the use of photomask to produce 2D convergence can be combined with additional shaping in the $3^{rd}$ dimension. One method of accomplishing this is a layer-by-layer photolithographic production of two additional converging surfaces in the $3^{rd}$ dimension. Alternatively, a 2D converging insertion tip of a probe may be further isotropically etched to produce two additional converging surfaces.

BRIEF DESCRIPTION OF THE DRAWINGS

The accompanying drawings, which are incorporated into and form a part of the disclosure, are as follows:

FIG. 1 is an exploded isometric view of an exemplary embodiment of the spine-reinforced microelectrode array probe of the present invention, with the spine spanning substantially the full length of the probe body, and illustrating the assembly and attachment of the separately fabricated components.

FIG. 2 is a cross-sectional view taken along the line 2-2 in FIG. 1 illustrating the thin film construction of the elongated probe body having a plurality of conductive lines enclosed within a polymeric material.

FIG. 3 is an isometric view of the embodiment of FIGS. 1 and 2 as assembled, and illustrating the fixed attachment of the pre-fabricated rigid body support, i.e. spine, to the elongated probe body.

FIG. 4 is a cross-sectional view taken along the line 4-4 in FIG. 3 illustrating the thin film construction of the assembled microelectrode array probe.

FIG. 7 also shows electrodes on opposite surfaces of the probe body.

FIGS. 13-24 show an exemplary method of fabrication the microelectrode array probe of the present invention, particularly having a reinforced insertion section and a non-reinforced flexible cable section that is integrally connected to the insertion section as a monolithic formation.

DETAILED DESCRIPTION

Figure 5:
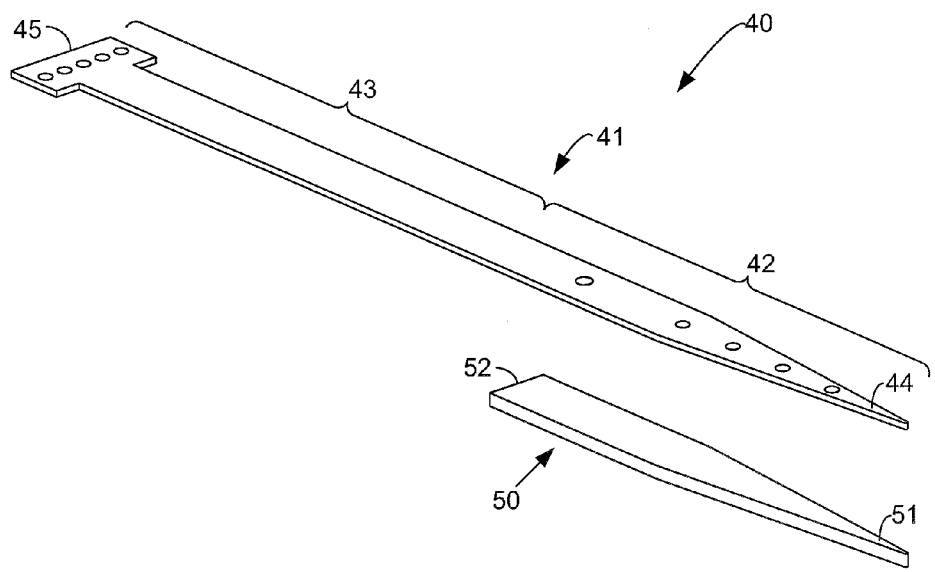
FIG. 5 is an exploded isometric view of another exemplary embodiment of the spine-reinforced microelectrode array probe of the present invention, with the spine having a length shorter than the probe body so that only an insertion section of the probe body is reinforced, while a cable section of the probe body remains unreinforced and flexible.

Turning now to the drawings, FIG. 1 shows an exploded isometric view of a first exemplary embodiment of the spine-reinforced microelectrode array probe of the present invention, generally indicated at reference character 10. The probe is shown as a single shank probe, having two main components, (1) an elongated probe body 11 which has an electrically-insulating material construction enclosing a plurality of conductive lines (and therefore also characterizable as an insulating probe body, a polymeric probe body if insulating polymers are used, or a flexible probe body if elastomeric insulating materials are used), and (2) a rigid spine (also characterized as an insertion shank) 30. Both the probe body 11 and the rigid spine 30 have an elongated configuration extending between respective opposing ends. In particular, the probe body 11 has an insertion end 12 with a pointed insertion tip 13 and an opposite connector end 14, and the rigid spine 30 has an insertion end 31 with a pointed insertion tip 32 and an opposite base end 33. While a single shank probe is shown in FIG. 1 to illustrate the features of the present invention, the present invention may also be realized and implemented as multi-shank probes. For such multi-shank embodiments, it is appreciated that the shanks are typically arranged in parallel and connected to a common base. Furthermore, each probe shank may have one or more contacts or exposed electrodes or leads.

Microelectrodes 15-19 are shown located along the probe body 11 suitably near the insertion end 12. In particular, the microelectrodes are shown exposed through a top surface 28 of the probe body 11. And leads 20 are formed at the connector end 14 of the probed body for connecting to a connector, such as a percutaneous connector (not shown). Connecting the leads 20 to the respective microelectrodes 15-19 are the conductive lines (not shown) also characterized as wire traces. FIG. 2 is a cross-sectional view taken along the line 2-2 in FIG. 1 illustrating the thin film construction of the elongated probe body 11 and the particular electrical connection of microelectrode 15. As shown, two insulating layers 25 and 27 surround a conductive line, represented by bond pad 29. The electrode 15 is shown connected to the bond pad 29 and exposed at a top surface 28 through a via in the polymer layer 27. The microelectrode material may be, for example, activated iridium metal. And the spine 30 is shown spanning substantially the full length of the probe body, and illustrating the assembly and attachment of the separately fabricated components. As can be seen in FIG. 1 both the polymer probe body 11 and the rigid spine 30 were fabricated and released as separate components prior to being joined as shown. For the spine, foils of various thicknesses may be used, such as for example, 15, 25, or 50 um thick titanium foils.

FIGS. 3 and 4 show the elongated probe body 11 and the rigid spine 30, subsequently joined and assembled together along an upper surface 34 of the spine and a lower surface 26 of the probe body. In particular, FIG. 3 is an isometric view of the embodiment of FIGS. 1 and 2 as assembled, and illustrating the fixed attachment of the pre-fabricated rigid spine 30, to the elongated probe body. And FIG. 4 is a cross-sectional view taken along the line 4-4 in FIG. 3 illustrating the thin film construction of the assembled microelectrode array probe through microelectrode 15. Preferably a bond or adhesive 36 is used to fixedly attach the two together. The adhesive may be either a type which produces a permanent bond, or a temporary one. For example, in one exemplary embodiment the adhesive used is a bio-adhesive (such as polysaccharide) of a type which loses its adhesion properties (e.g. dissolves) when placed in the body, so that the rigid spine only may be removed after insertion while the polymer probe body remains implanted.

Figure 6:
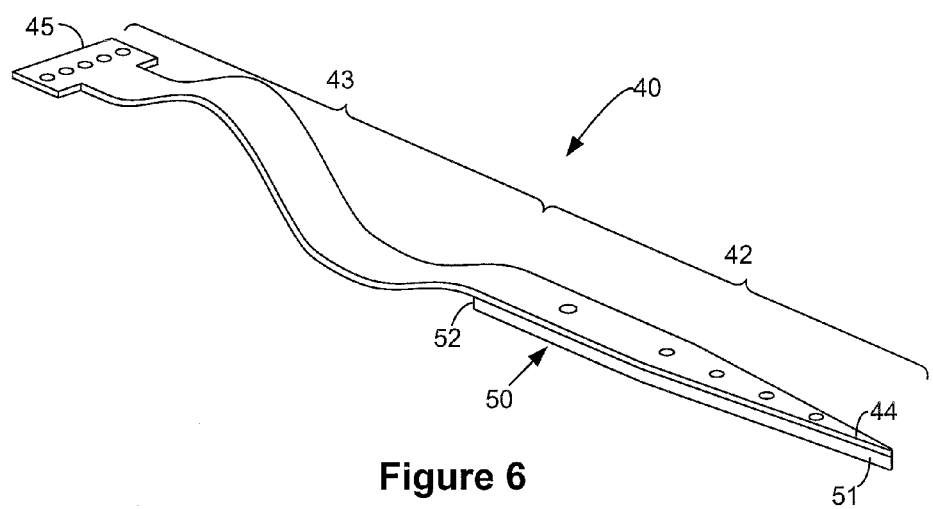
FIG. 6 is an isometric view of the embodiment of FIG. 5 as assembled, and illustrating the rigidity of the insertion section of the probe body due to structural reinforcement by the spine, and the flexibility of the cable section.

FIG. 5 is an exploded isometric view of a second exemplary embodiment of the spine-reinforced microelectrode array probe of the present invention, generally indicated at 40, having an elongated probe body 41 extending between an insertion end 44 and a connector end 45, and attached to a spine 50 which has a length shorter than the probe body. In particular, the length of the spine 50 is shown substantially equivalent to an insertion section 42 of the probe body. The spine is shown aligned with the probe body with an insertion tip 51 adjacent the insertion tip 44 of the probe body. And a trailing end 52 of the spine demarcates the transition from the insertion section 42 to the cable section 43. And FIG. 6 is an isometric view of the embodiment of FIG. 5 as assembled, and illustrating the rigidity of the insertion section of the probe body due to structural reinforcement by the spine, and the flexibility of the cable section. Attached in this manner, the spine only reinforces the insertion section of the probe body, while the cable section 43 of the probe body remains unreinforced and flexible (if an elastomeric insulating material is used).

Figure 7:
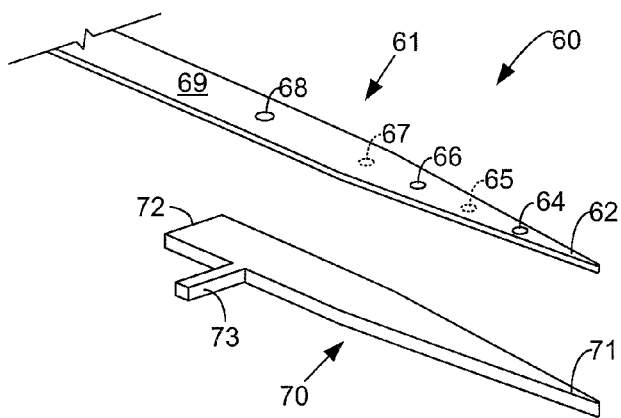
FIG. 7 is an exploded isometric view of another invention of the present invention, having a spine that includes a tab for use as a handle to remove the spine after insertion and implantation of the probe body.
Figure 9:
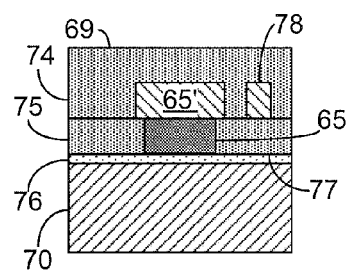
FIG. 9 is a cross-sectional view taken along the line 9-9 in FIG. 8 illustrating the thin film construction of the assembled microelectrode array probe through microelectrode 65.
Figure 8:
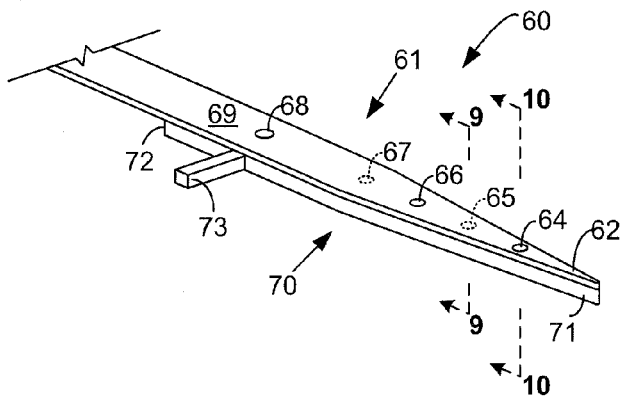
FIG. 8 is an isometric view of the embodiment of FIG. 7 as assembled, and illustrating the rigidity of the insertion section of the probe body due to structural reinforcement by the spine, and the flexibility of the cable section when an elastomeric insulating material is used to surround the conductive lines.
Figure 10:
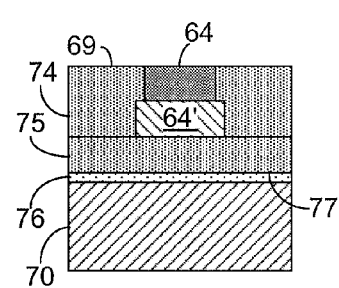
FIG. 10 is a cross-sectional view taken along the line 10-10 in FIG. 8 illustrating the thin film construction of the assembled microelectrode array probe through microelectrode 64.

FIG. 7 is an exploded isometric view of another embodiment of the microelectrode array probe of the present invention, indicated at 60, and having a spine 70 that includes a tab 73, which may be near a trailing end 72 of the spine, for use as a handle to remove the spine after insertion and implantation of the probe body 61. And FIG. 8 is an isometric view of the embodiment of FIG. 7 as assembled, and FIGS. 9 and 10 show cross-sections of the embodiment take along lines 9-9 and 10-10, respectively. FIGS. 7-10 together illustrate several concepts of the present invention. First, the probe body 61 is shown having microelectrode contacts on both top and bottom surfaces 69 and 77 of the probe body 61. In particular, microelectrodes 64, 66, and 68 are exposed through the top surface 69, while electrodes 65 and 67, shown as dotted lines, are exposed through the bottom surface 77. For example, electrode 64 is shown exposed through top surface 69 as shown in FIG. 10, and electrode 65 is shown embedded in the probe adjacent lower surface 77 as shown in FIG. 9. Similar to FIGS. 2 and 4, bond pads 65' and 64' are shown connecting the respective electrodes to conductive lines and leads at a connector end, not shown. And two polymeric layers 74 and 75 are shown surrounding/enclosing the bond pads. When the spine 70 is fixedly attached and connected to the probe body 61, the upper electrode contact 64 is exposed, while the lower electrode contact 65 is embedded and only exposed upon removal of the spine. Only after the bond or adhesive 76 loses its bonding/adhesion properties, may the spine 70 be removed, using the tab 73.

Figure 11:
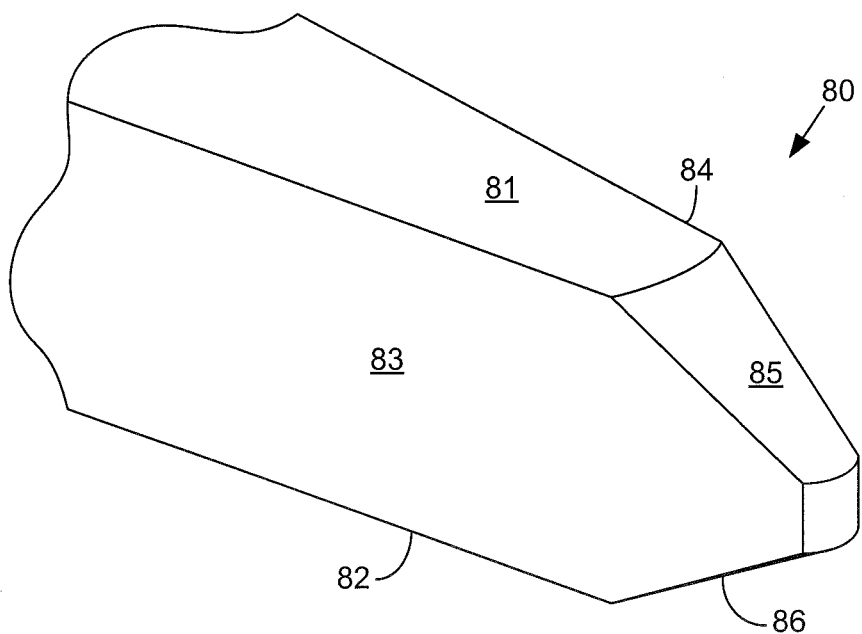
FIG. 11 is an enlarged perspective view of an insertion tip of the present invention that is fabricated with four three-dimensionally converging faces.
Figure 12:
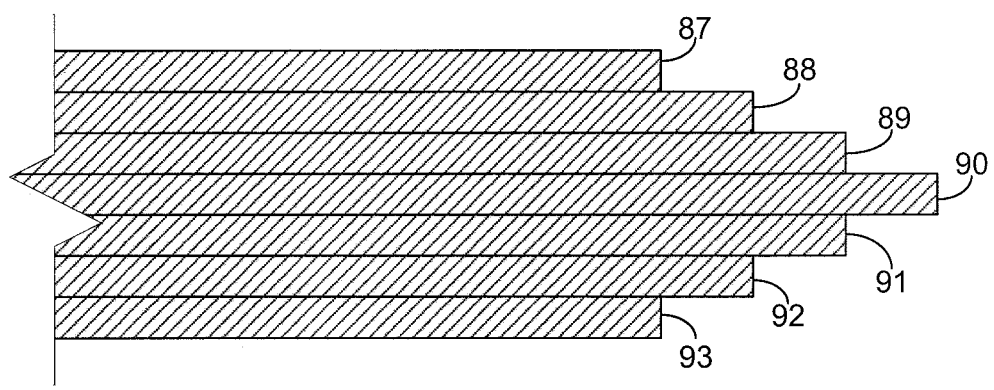
FIG. 12 is one illustrative method of producing the 3D converging faces, using staggered thin film layers.

FIG. 11 shows an insertion tip 80 of a spine embodiment of the present invention. The tip 80 is shown having two side converging faces 84 and 82, which may be formed by etching a 2D convergence pattern. The tip 80 is also shown having two additional top and bottom convergence faces 84 and 86 to provide another ($3^{rd}$) dimension of convergence, and thereby increase the sharpness of the insertion tip 80. Various methods may be used, such as for example employing thin film fabrication techniques, i.e. using layer-by-layer photolithographic production of two additional converging surfaces in the $3^{rd}$ dimension. This is illustrated in FIG. 12 where the layers 87-93 of the spine material are staggered at the insertion end, between a top layer 87 and a bottom layer 93. Alternatively, a 2D converging insertion tip of a probe may be further isotropically etched to produce two additional converging surfaces.

FIGS. 13-26 together show a first exemplary fabrication method of microelectrode arrays of the present invention having a spine reinforced insertion section and a non-reinforced cable section, capable of flexing especially if constructed using an elastomeric material. The insertion section and the cable section are monolithically formed so as to be integrally connected, and so that no additional connecting step is necessary. Generally, the process uses a spine substrate on which the probe body is fabricated, such as using photolithography. Subsequently, a section of the spine substrate is removed, so that an adjacent section of the polymer probe body is free to flex.

In particular, FIGS. 13A and B show top and cross-sectional views, respectively, of a first layer provided in a first exemplary embodiment of the fabrication method of the present invention, and in particular showing a silicon carrier substrate 100 upon which the probe is fabricated, including the connection between the spine and the probe body. The carrier substrate can be composed of but not limited to silicon (semiconductor), glass (insulator) and/or metal (conductor) material. FIGS. 14A and B next show a release layer 101 (e.g. 5 μm of photoresist) deposited on the silicon substrate. Thicknesses can range from a few nanometers to several hundred microns.

FIGS. 15A and B show top and cross-sectional view, respectively, of the multilayer following FIG. 14, after attaching a rigid material substrate 102 (such as titanium) which will become the spine of the probe. The combined material can be subjected to a temperature cycle in an open environment or under vacuum and/in a nitrogen filled environment or any combination thereof. The silicon carrier substrate 101 serves as a rigid material and prevent damage to the thin titanium substrate 102 due to processing.

FIGS. 16A and B show top and cross-sectional view, respectively, of the multilayer following FIG. 15, after depositing and patterning a sacrificial layer 103 over the spine substrate 102. The sacrificial layer may be but is not limited to photoresist, which will be used as the release layer in a subsequent step. Additionally, the sacrificial layer acts as barrier for a laser ablation process or deep reactive ion etch or wet chemical etch that defines the shape and size of the spine substrate without damaging the flexible polymer cable portion of the device.

FIGS. 17-21 next illustrate the fabrication of the elongated probe body portion. In particular, FIGS. 17A and B show an insulating film 104, e.g. a polymer film like but not limited to Parylene, polyimide and silicone deposited onto the surface of the attached spine substrate. The deposited polymer film can range from a few nanometers to several hundred of microns. And FIGS. 18A and B show top and cross-sectional view, respectively, of the multilayer following FIG. 17, after depositing and defining a conductive material, which can consist of several layers of different metal layers, onto the surface of the polymer film. The conductive material is represented by bond pads 105. The conductive material can be deposited using a variety of the methods like but not limited to spin, spray, screen or metal printing, sputtering, electroplating and/or evaporation techniques. The thickness of the film deposited can range from a few nanometers to several millimeters. The film is then placed under a temperature curing cycle if necessary. Next, in FIGS. 19A and B, a second polymer film layer 108 is deposited which may be composed of a similar material as that of the first polymer film layer 104. Preferably the first polymer film is provided with adhesion treatment, as known in the art, prior to depositing the second polymer film layer, to improve adhesion/bonding therebetween. The thickness of the film deposited can range from a few nanometers to several millimeters. The bond pad and electrode openings in the polymer film may be defined all the way down to the conductive material by using dry (deep) reactive ion etch or wet chemical etch techniques.

FIGS. 20A and B show top and cross-sectional view, respectively, of the multilayer following FIG. 19, after patterning the overall shape and pattern 109 of the titanium based microelectrode arrays into the polymer film layers using dry (deep) reactive ion etch or wet chemical etch techniques. The dry (deep) reactive ion etch or wet chemical etch should etch all the polymer layers all the way down to the surface of a titanium substrate. In FIGS. 21A and B, the microelectrode material 110 like but not limited to iridium oxide, platinum, platinum iridium, doped diamond, etc. is deposited onto the electrode portions of the device using electroplating techniques. The thickness of the iridium oxide can range from a few nanometers to several hundred microns. A sacrificial material may be used to define the Iridium location on the microelectrodes. Various methods of depositing the thin film iridium metal may be employed, including for example sputtering and evaporation. In one embodiment, approximately 250 nm of iridium was deposited. Furthermore, the thin film iridium metal may then be preferably activated to convert the thin film iridium to thin film iridium oxide using voltage cycling in a physiological saline solution.

Figure 22B:
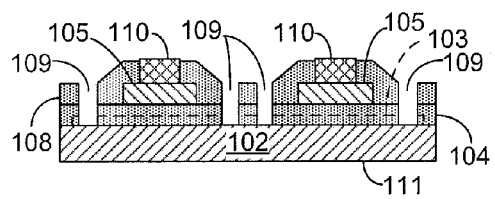
Figure 22A:
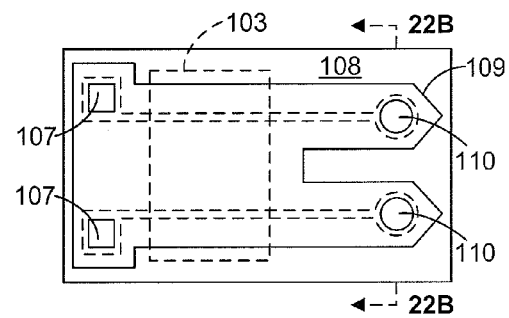
Figure 23B:
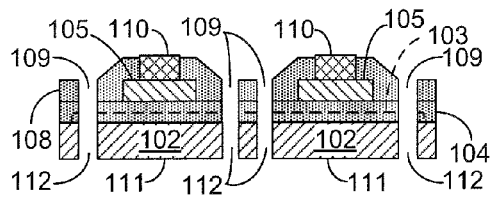
Figure 23A:
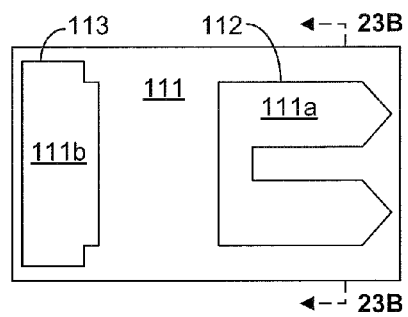
Figure 24B:
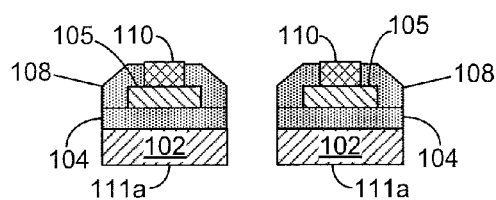
Figure 24C:
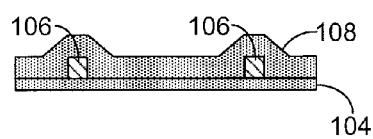

FIGS. 22-24 show a first example method of patterning the titanium substrate and releasing the array, following FIG. 21. In FIGS. 22A and B, the attached titanium substrate is then immersed into a solution that will dissolve or etch away the release layer 103. This will allow the separation of titanium substrate 102 from the carrier substrate 101. And in FIGS. 23A and B, the spine regions 111a and 111b of the device are defined on the backside by patterns 112 and 113 produced using laser, (deep) reactive ion, or wet chemical etch techniques on the backside of the titanium substrate as shown in FIG. 1.K. This is the step that uses the sacrificial layer 103 deposited above that will protect the flexible cabling portion of the device.

Figure 24A:
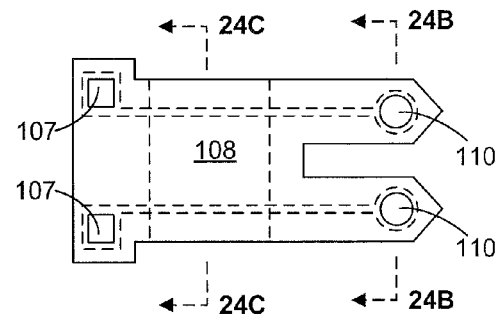

In FIGS. 24A and B, the titanium substrate 102 is immersed into a solution that will dissolve or etch away the remaining sacrificial layer thus releasing the device. FIGS. 24A, B, and C show a top view, a cross-sectional view through the electrodes, and a cross-sectional view through the conductive lines, respectively, of the multilayer following FIG. 23, after immersing in a solution to remove the sacrificial layer and release microelectrode array. As can be seen, there are three distinct regions, including a rigid insertion section, a rigid connector section where leads 107 are shown, and a flexible cable region between the insertion and connector regions.

Another way of characterizing the probe of FIG. 24 is that it includes a first rigid spine layer, with a second rigid spine layer at a removed location from the first rigid spine layer. The first and second rigid spine layers are integrally formed as part of a monolithic rigid spine layer that is subsequently separated from each other by removing a mid section of the monolithic rigid spine layer connecting between the first and second rigid spine layers. A first insulating layer has a first end section formed on the first rigid spine layer, a second end section formed on the second rigid spine layer, and a mid section formed on a sacrificial layer previously formed between the mid section of the first insulating layer and the mid section of the monolithic rigid spine layer, but which is now removed to effect the removal of the mid-section of the monolithic rigid spine layer. Also, the probe includes a plurality (i.e. an array) of at least one conductive line formed on the first insulating layer so that each conductive line extends across the mid section of the first insulating layer and terminates at conductive pads formed at the first and second end sections. A second insulating layer is formed over the array to surround and insulate the array while leaving the conductive pads exposed. In this manner, the first rigid spine layer rigidly supports the conductive pads formed at the first end section, the second rigid spine layer rigidly supports the conductive pads formed at the second end section, and sections of the array, the first insulating layer, and the second insulating layer that are located along the mid-section of the first insulating layer are flexible.

Figure 25B:
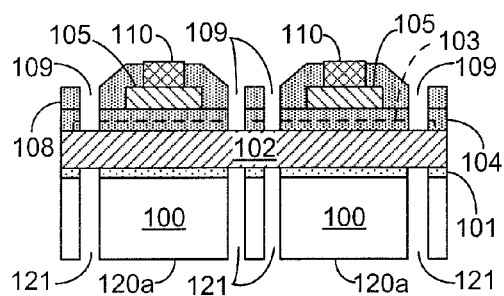
FIGS. 25 and 26 show two alternative method steps to the steps shown in FIGS. 22 and 23, respectively.
Figure 25A:
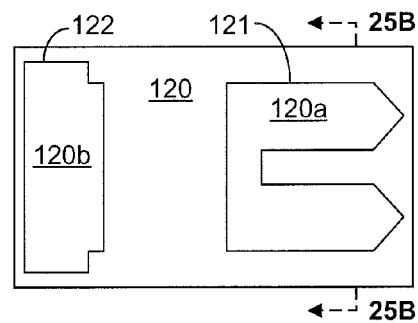
Figure 26B:
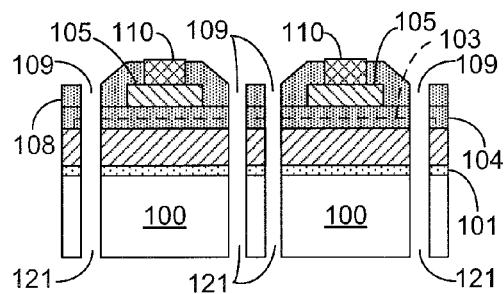
Figure 26A:
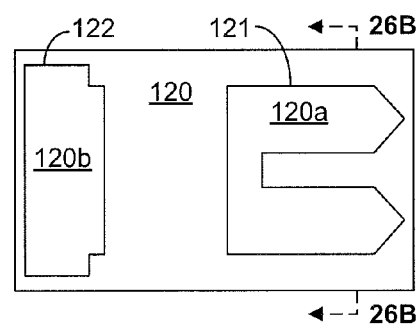

And FIGS. 25 and 26 show a second example method of patterning the spine substrate 102 and releasing the array probe, that is different from FIGS. 22 and 23. In particular, FIGS. 25A and B show top and cross-sectional view, respectively, of a multilayer formed in a second exemplary embodiment of the fabrication method of the present invention, after performing steps shown in FIGS. 13-21 as described above, and further defining and etching away backside of substrate and release layer using wet and/or dry etch techniques. In FIGS. 25A and B, the backside of the carrier substrate is defined and etched using wet or dry etch techniques. The substrate material should be etched all the way down to the titanium substrate. A protective film can be used on the top surface of the titanium substrate in order to protect it from the wet or dry etch techniques used in this step and subsequent steps. FIGS. 26A and B show top and cross-sectional view, respectively, of the multilayer following FIG. 25, after etching away titanium substrate from backside of carrier substrate using wet or dry etch techniques. In FIGS. 26A and B the titanium regions of the device are defined using wet or dry etch techniques. A last step following FIG. 26 is the same as FIG. 24, where the attached titanium substrate is immersed into a solution that will remove any protective layer used in previous steps, remove the release layer and remove the sacrificial layer thus releasing device.

While particular operational sequences, materials, temperatures, parameters, and particular embodiments have been described and or illustrated, such are not intended to be limiting. Modifications and changes may become apparent to those skilled in the art, and it is intended that the invention be limited only by the scope of the appended claims.

We claim:
1. A microelectrode array probe comprising:
an elongated probe body having a plurality of conductive lines enclosed within an electrically insulating material and extending from a connector end of the probe body toward an insertion end of the probe body, and a plurality of microelectrodes connected by the plurality of conductive lines to corresponding leads at the connector end; and an elongated rigid spine fixedly connected to the probe body to structurally reinforce the probe body, wherein the elongated rigid spine is fixedly bonded to the probe body with a bio-adhesive that dissolves in a body so that the spine may be removed after probe insertion.

2. The microelectrode array probe of claim 1, wherein the bio-adhesive is polysaccharide.

3. The microelectrode array probe of claim 1, wherein the spine has a tab for removing the spine upon being subsequently detached from the elongated probe body.

4. The microelectrode array probe of claim 1, wherein the at least one of the microelectrodes is formed on a connection surface to which the spine is fixedly bonded, so as to be exposed only after the spine is detached.

* * * * *